(12) United States Patent
Rieske et al.

(10) Patent No.: US 9,675,729 B2
(45) Date of Patent: Jun. 13, 2017

(54) ACTIVE POLYMER LAYER MADE OF CHITIN DERIVATIVES, ESPECIALLY FOR A DRESSING, AND ITS USE

(71) Applicant: CELTHER POLSKA SP. Z O.O., Zakroczym (PL)

(72) Inventors: Piotr Rieske, Lodz (PL); Ewelina Stoczynska-Fidelus, Makow (PL); Karolina Skolucka, Sosnowiec (PL); Sylwester Piaskowski, Konstantynow (PL)

(73) Assignee: CELTHER POLSKA SP. ZO.O., Zakroczym (PL)

( * ) Notice: Subject to any disclaimer, the term of this patent is extended or adjusted under 35 U.S.C. 154(b) by 0 days.

(21) Appl. No.: 14/423,404

(22) PCT Filed: Aug. 20, 2013

(86) PCT No.: PCT/PL2013/000105
§ 371 (c)(1),
(2) Date: Feb. 23, 2015

(87) PCT Pub. No.: WO2014/031017
PCT Pub. Date: Feb. 27, 2014

(65) Prior Publication Data
US 2015/0182657 A1   Jul. 2, 2015

(30) Foreign Application Priority Data
Aug. 24, 2012 (PL) ......................................... 400509

(51) Int. Cl.
*A61L 15/28* (2006.01)
*A61L 15/42* (2006.01)
*A61L 15/44* (2006.01)

(52) U.S. Cl.
CPC ............. *A61L 15/28* (2013.01); *A61L 15/425* (2013.01); *A61L 15/44* (2013.01);
(Continued)

(58) Field of Classification Search
CPC ........ A61L 15/28; A61L 15/425; A61L 15/44; A61L 2300/404; A61L 2300/412; A61L 2300/802; A61L 2430/34
See application file for complete search history.

(56) References Cited

U.S. PATENT DOCUMENTS 4,485,096 A    11/1984  Bell
4,699,135 A *  10/1987  Motosugi ................ A61L 15/28
                                                            424/400

(Continued)

FOREIGN PATENT DOCUMENTS

JP   2011167237 A     9/2011
PL   WO2005/099781 *  10/2005  ............. A61L 15/22
WO   2005099781 A1   10/2005

OTHER PUBLICATIONS

Hu et al., "Protein adsorption, fibroblast activity and antibacterial properties of poly(3-hydroxybutyric acid-co-3-hydroxyvaleric acid) grafted with chitosan and chitooligosaccharide after immobilized with hyaluronic acid," Biomaterials 24 (2003) 2685-2693.
(Continued)

*Primary Examiner* — Sean Basquill
(74) *Attorney, Agent, or Firm* — Brooks Kushman P.C.

(57) ABSTRACT

The invention refers to an active polymer layer (1) especially for a dressing of a three-dimensional structure characterized in that it has non-fibrous structure made of chitin derivatives obtained in the esterification reaction of chitin in the presence of aliphatic anhydrides of a chain of a length from C2 to C8 straight saturated, and anhydrides preferably, acetic-propionic anhydride, butanoic-propionic anhydride, branched unsaturated anhydrides preferably, methacrylic
(Continued)

anhydride, 2-butenoic anhydride and cyclic preferably, maleic anhydride, succinic anhydride, phthalic anhydride) and hydroxyacids preferably, lactic acid, glycolic acid, which can comprise additionally fibroblasts (6) and/or keratinocytes (7) and is used for producing dressing which can be applied on affected areas, including clean, flat shallow ulcerations characterised by modifiable granulations, the patent femoral artery with mild and moderate deficiency and no intensive exudation.

17 Claims, 5 Drawing Sheets

(52) U.S. Cl.
CPC ... *A61L 2300/404* (2013.01); *A61L 2300/412* (2013.01); *A61L 2300/802* (2013.01); *A61L 2430/34* (2013.01)

(56) References Cited

U.S. PATENT DOCUMENTS

| | | | |
|---|---|---|---|
| 5,106,949 A | 4/1992 | Kemp et al. | |
| 5,536,656 A | 7/1996 | Kemp et al. | |
| 2009/0010982 A1* | 1/2009 | Abrahams | A61F 13/02 424/422 |
| 2011/0021964 A1* | 1/2011 | Larsen | A61L 26/0066 602/47 |

OTHER PUBLICATIONS

Ueno et al., "Accelerating effects of chitosan for healing at early phase of experimental open wound in dogs," Biomaterials 20 (1999) 1407-1414.
Ishihara et al., "Photocrosslinkable chitosan as a dressing for wound occlusion and accelerator in healing process," Biomaterials 23 (2002) 833-840.
Cho et al., "Water-soluable chitin as a wound healing accelerator," Biomaterials 20 (1999) 2139-2145.
Obara et al., "Photocrosslinkable chitosan hydrogel containing fibroblast growth factor-2 stimulates wound healing in healing-impaired db/db mice," Biomaterials 24 (2003) 3437-3444.
Mi et al., "Control of wound infections using a bilayer chitosan wound dressing with sustainable antibiotic delivery," J Biomed Mater Res 59:438-499, 2002.
Mao et al., "he properties of chitosan-gelatin membranes and scaffolds modified with hyaluronic acid by different methods," Biomaterials 24 (2003) 1621-1629.
Muzzarelli et al., "The biocompatibility of dibutyryl chitin in the context of wound dressings," Biomaterials 26 (2005) 5844-5854.
Madihally et al., "Porous chitosan scaffolds for tissue engineering," Biomaterials 20 (1999) 1133-1142.
Chilarski et al., "Novel Dressing Materials Accelerating Wound Healing Made from Dibutyrylchitin," Fibres & Textiles in Eastern Europe Oct./Dec. 2007, vol. 15, No. 4 (63).
Witkowski et al., "Topical Metronidazole Gel the Bacteriology of Decubitus Ulcers," Pharmacology and Therapeutics, Sep. 1991, vol. 30, No. 9, p. 660-661.

* cited by examiner

ACTIVE POLYMER LAYER MADE OF CHITIN DERIVATIVES, ESPECIALLY FOR A DRESSING, AND ITS USE

CROSS-REFERENCE TO RELATED APPLICATION

This application is the U.S. national phase of PCT Application No. PCT/PL2013/000105 filed on Aug. 20, 2013, which claims priority to Poland Patent Application No. PL 400509 filed on Aug. 24, 2012, the disclosures of which are incorporated in their entirety by reference herein.

A subject of the invention is an active polymer layer made of chitin derivatives, especially for a dressing and its use for producing the dressing used to care of wounds and ulcerations, accelerating healing of wounds, such as:
- clinically infected wounds,
- slow healing wounds: pressure ulcers, crural ulceration, varicose veins, diabetic gangrene, burns, abscesses, boils, whitlows, after nail removal
- wounds exudating copiously or moderately, at the final part of the cleaning stage and with new tissue being formed,
- ulcerations;

and for dressing of wounds and in clinical cases requiring a special dressing material, including:
- lacerations, contused wounds, abrasions, crural ulceration, burns, chemical burns, radiation injuries,
- in transplant treatment, for covering areas where grafts were collected or applied
- in plastic and cosmetic surgery to treat keloids,
- in amputations and reconstruction treatment requiring reconstruction of tissues.

The dressing according to the invention is particularly useful in cases meeting the following requirements: clean, flat, shallow ulcerations, presence of modifiable granulation, the patent femoral artery with mild and medium deficiency, no intensive exudation. The dressing can be used in humans, as well as for veterinary applications.

Chitin derivatives (chitin polyesters) are obtained in a reaction of chitin esterification in a presence of relevant aliphatic and cyclic anhydrides, and certain hydroxy acids. Chitin, with previously removed calcium carbonate, is subjected to acylation in a presence of a selected catalyst (being at the same time the reaction medium) and selected anhydride or hydroxy acid. Chitin can be subjected to esterification both in one and in two locations.

Substituents may be derivatives of hydroxy acids (e.g., lactic acid, glycolic acid), straight-chain saturated aliphatic anhydrides (length of the acid residue chain from C2 to C8, e.g., from acetic anhydride to octane anhydride, and from anhydrides such as acetic-propane anhydride, butane-propane anhydrides), branched-chain aliphatic unsaturated anhydrides (e.g., methacrylic anhydride, 2-butene anhydride) or cyclic anhydrides (maleic anhydride, glutar anhydride, succinic anhydride, phthalic anhydride). Chitin may be substituted in one or two locations using one or two substitutes of the same or different chain length.

In case of leaching, the term "chitin derivatives" is understood as chitin polyesters produced in the chitin esterification reaction in a presence of a selected catalyst and a straight-chain saturated aliphatic anhydride, with the acid-residue chain of C2 to C8 (e.g. from acetic anhydride to octane anhydride and from anhydrides, such as: acetic-propionic anhydride, butanoic-propionic anhydride), aliphatic branched unsaturated anhydrides (e.g. methacrylic anhydride, 2-butenoic anhydride) or cyclic anhydrides (glutaric anhydride, succinic anhydride, phthalic anhydride).

Chitin and chitosan act as chemoattractants for macrophages or neutrophils, thus initiating healing processes, and stimulating granulating and re-epithelisation processes. It limits formation of scars and, this being its significant advantage over competitive polymer meshes—it has an internal antibacterial effect, simultaneously allowing binding and controlled release of exogenous antibacterial factors [Hu S G, Jou C H, Yang M C.: Biomaterials 2003; 24:2685; Ueno H, et al.: Biomaterials 1999; 20:1407; Ishihara M, et al.: Biomaterials 2002; 23:833; Cho Y W, et al.: Biomaterials 1999; 20: 2139; Obara K, et al.: Biomaterials 2003; 24:3437; Mi F L, et al.: Biomed Mater Res 2002; 59:438; Mao J S, et al.: Biomaterials 2003; 24:1621; Muzzarelli R A, et al. Biomaterials 2005; 26:5844]. Furthermore, chitin and its derivatives have intrinsic antibacterial and antifungal properties [Hu S G, Jou C H, Yang M C.: Biomaterials 2003; 24:2685]. The precise mechanism underlying those properties has not been fully explained, however, numerous mechanisms possibly responsible for that phenomenon have been proposed. Cationic groups bound to anions of a bacterial cell wall may inhibit biosynthesis, moreover, chitin may disrupt molecular transport through a bacterial cell wall thus accelerating their death [Hu S G, Jou C H, Yang M C. Biomaterials 2003; 24:2685].

Advantages of chitin and its derivatives application in regenerative medicine:
- biocompatibility,
- induces intercellular reactions and tissue development,
- has appropriate mechanical and physical properties,
- biodegradable—at adequate rate—not exceeding reforming and without inducing immunoreaction; products of its degradation are nontoxic. The process is based on enzymatic hydrolysis of acetyl residues. A basic enzyme responsible for in vivo chitin degradation is lysozyme,
- appropriately controls behaviour of cells—adhesion, proliferation, migration, differentiation (it is possible for the polymer to bind with adhesive proteins and growth factors),
- ability to mobilise relevant cells in a surrounding tissue, responsible for repair processes, including stem cells.

Recently attempts have been made to furnish various medical implants with antibacterial properties through chemical or physical binding with antibiotics. Binding antibiotics with biomaterials aims at providing them with bacteriostatic or antiseptic properties, therefore, ensuring protection against infection. Use of immobilised (bound) medications is of significance for construction of biomaterials for treatment of slow healing wounds and ulcerations.

Polysaccharides have attracted significant interest as carriers of medications. In a living body, they are slowly dissolved by body fluids, therefore ensuring gradual release of a medicinal product in time.

In modern biomaterial designs tissue compatibility of biopolymers and their biodegradation capacities are used. Correct use of those properties may ensure a controlled release of medicines, dose optimising for a specific therapy and maintenance of an adequately high local medicine concentration for a maximum length of time.

The regeneration medicine seeks new alternate solutions, changing the approach to the treatment and filling of tissue defects. Properties of chitin and its derivatives, as natural polysaccharides, predestine them for immobilising of cells, enzymes and proteins, as well as for use as films in systems for controlled medicine release.

Chitin is cationic, and that is mainly responsible for electrostatic binding with anionic glucosamine glycans (GAG), proteoglycans and other negatively charged molecules. This characteristic of the biopolymer allows trapping and concentration of various biomolecules, as numerous cytokines/growth factors are bound to GAG [Madihally S V, Matthew H W T.: *Biomaterials* 1999; 20:1133].

Wound dressings based on chitin or chitosan are known, e.g., as in the Japanese application JP2011167237, concerning a dressing based on nanofibres of chitin, chitosan or its composites, which is prepared only in water.

So far known dressings prepared on the base of chitosan or chitin showed good biologic properties in the contact with the wounds difficult to be healed. For improvement of the therapeutic properties, chitosan or chitin was replaced by chitin derivative, e.g. dibutyryl chitin. Such dressing is known from the Polish patent application PL367163 (WO2005/099781A1), which describes a wound dressing which uses dibutyryl chitin and chitin regenerated from dibutyryl chitin used to produce the wound dressing, and includes a method for its production. Those dressings are based on the spinning technology. The textile dressings require:

- plant for spinning fibres in the wet process or by electro-spinning on spinning machines,
- preparing of spinning solutions, polymer solidification, its washing, stretching, drying, etc.,
- cutting of those fibres, and their carding on special machines, and that process is accompanied by considerable loss of the polymer in form of dust,
- mat forming on special machines, its needle-punching and heat processing to obtain the final nonwoven form.

Unexpectedly it appeared that formation of the active polymer layer from different chitin derivatives obtained in the esterification reaction of chitin in the presence of aliphatic anhydrides of a chain of a length from C2 to C8 straight saturated, branched unsaturated, cyclic anhydrides in the non-fibrous form allows for obtaining even better healing properties, higher speeds of skinning over, viability, bonding force to polymer than known dressing materials.

Moreover, comparative studies of the dressings containing active layers on the base of dibutyrylochitin (DBC) in the fibrous and non-fibrous form (prepared according to the invention) showed significant differences between a bonded product made of DBC and dressings according to the invention. The dressings comprising non-fibrous active polymer layer on the base of chitin derivatives with applied cells deserves special attention, because on used so far chitin derivatives has not managed to apply cells and they have not found practical use. Such results were achieved, among others, using specified in the invention polymer mixtures.

The subject of the invention is an active polymer layer especially for a dressing of a three-dimensional structure, characterized in that, it has non-fibrous structure made of chitin derivatives obtained in the esterification reaction of chitin in the presence of aliphatic anhydrides of a chain of a length from C2 to C8 straight saturated, and anhydrides, preferably acetic-propionic anhydride, butanoic-propionic anhydride, branched unsaturated anhydrides, preferably methacrylic anhydride, 2-butenoic anhydride and cyclic anhydride, preferably maleic anhydride, succinic anhydride, phthalic anhydride and hydroxyacids, preferably lactic acid, glycolic acid.

Preferably, active polymer layer is characterized in that chitin derivatives produced in the chitin esterification reaction in presence of straight-chain saturated aliphatic, with the chain of C2-C8 anhydrides of branched-chain unsaturated and cyclic and selected hydroxy acids are mono- or disubstituted.

Preferably, active polymer layer is characterized in that disubstituted chitin derivatives contain substitutes of the same chain lengths.

Preferably, active polymer layer is characterized in that disubstituted chitin derivatives contain substitutes of different chain lengths.

Preferably, the active polymer layer is made of one chitin derivative, at a ratio from 0.1 to 100%, or a mixture of at least two chitin derivatives.

Preferably, the active polymer layer is porous.

Preferably, the active polymer layer is non-porous.

Preferably, the active polymer layer has pores of 0.1 mm to 4.0 mm in diameter, straight or coiled, depending on a wound type, or pores of a various size, in a single dressing ranges the pores percentage ratio from 1-90%.

Preferably, the active polymer layer is obtained by leaching.

Preferably, the active polymer layer is characterized in that in the leaching method the water-soluble porogenic substance is uniformly spread, $$\left(\frac{\text{weight\_of\_polymer}}{\text{weight\_of\_porogenic\_agent}} = \text{from } \frac{1}{5} \text{ to } \frac{1}{40}\right),$$

with crystals of 100 to 800 µm in a mould, and then a solution of polymer selected from a group of chitin derivatives or mixture of chitin derivatives dissolved in an organic solvent is applied, and then the solvent is evaporated at 24° C.-80° C., for 3-20 h, while the process of washing out the porogenic substance and solvent residues is done with water, for 1-24 h.

Preferably, the active polymer layer is characterized in that as the porogenic substance sodium chloride (NaCl) is used.

Preferably, the active polymer layer is characterized in that as the organic solvent ketone, alkyl alcohols are used.

Preferably, the active polymer layer is characterized in that a concentration of chitin derivative/mixture of chitin derivatives in solvent is 0.01-0.4 g/ml, preferably 0.001-0.15 g/ml.

Preferably, the active polymer layer is characterized in that it is obtained by dissolving of (0.1-99%) chitin derivative, or their mixture in the solution of lithium chloride (LiCl) (5-6%)-N,N-dimethylacetamide (DMAc), adding of calcium carbonate and mixing at reduced temperature, and then pouring out such prepared mixture to the mould, evaporating of the solvent and washing with the solution of hydrochloric acid, water and drying.

Preferably, active polymer layer is characterized in that calcium carbonate ($CaCO_3$) is used in the amount of 0.1-5%, preferably 1-3.5%, wherein the pores with different courses and 100-1000 µm sizes are obtained.

Preferably, the active polymer layer is characterized in that it is saturated with excipients.

Preferably, the active polymer layer is characterized in that as excipients silver ions $Ag^+$ (0.01-5%) are used, and/or potassium ions $K^+$ (0.01-2%), and/or calcium ions $Ca^{2+}$ (0.01-2%), and/or $Zn^{2+}$ ions (0.01-1.5%), and/or citric acid (0.001-5%), and/or bismuth salts (0.001-5%).

Preferably, the active polymer layer is characterized in that it is saturated with antiseptic substances.

Antibiotic molecules, depending on their size, are either trapped in the polymer network during the dressing production process, or are adsorbed on a surface.

Preferably, the active polymer layer is characterized in that as antiseptic substances are used: neomycin, polymyxin B, bacitracin, vancomycin, gentamycin, cephalosporin and other wide-spectrum antibiotics.

Preferably, the active polymer layer is characterized in that it is saturated with metronidazole.

Preferably, the active polymer layer is characterized in that it is spread on the hydrogel.

Preferably, the active polymer layer is characterized in that as hydrogel gelatin, agar, polyethylene glycol, polyacrylic acid are used.

Preferably, the active polymer layer is characterized in that it is placed inside hydrogel structure or on the hydrogel surface in the amount of 0.01-98% by weight per hydrogel volume, of a thickness of 0.01-1.5 mm.

Another subject of the invention is an active polymer layer especially for a dressing, which is characterized in that it has non-fibrous structure made of chitin derivatives obtained in the esterification reaction of chitin in the presence of aliphatic anhydrides of a chain of a length from C2 to C8 straight saturated, and anhydrides, preferably acetic-propionic anhydride, butanoic-propionic anhydride, branched unsaturated anhydrides preferably methacrylic anhydride, 2-butenoic anhydride and cyclic, preferably maleic anhydride, succinic anhydride, phthalic anhydride and hydroxyacids, preferably lactic acid, glycolic acid, and comprises fibroblasts and/or keratinocytes.

Another subject of the invention is a use of the active polymer layer for producing a dressing which can be applied on affected areas, including clean, flat shallow ulcerations characterised by modifiable granulations, the patent femoral artery with mild and moderate deficiency and no intensive exudation.

Preferably, the use of the active polymer layer for producing the dressing for use to the treatment of humans and in veterinary medicine.

The dressing containing the active polymer layer in accordance with the invention is characterised not only by relevant forming of chitin derivatives (three-dimensional structure). Also, disadvantageous parameters of the dressing comprising the active polymer layer formed solely of one chitin derivative, have been eliminated, including excessive brittleness, limited possibilities for making thick structures required for dressing of large defects or for dressings used for quick control of haemorrhages. Moreover, the bibliographic data show that combining wound dressing materials made of various plastics with medicines (antibiotics, cytostatics) and/or growth factors, chemotactic substances, increases effectiveness of the treatment. The dressing in accordance with the invention has numerous applications, including: cosmetic, treatment of ulcerations of various origins, treatment of burns, as well as in emergency medicine. The dressing in accordance with the invention has a safe and durable fixing (attaching, fastening) for veterinary applications.

The advanced form of the dressing comprising the active polymer layer in accordance with the invention, used for treatment of pressure, diabetic or vascular ulcerations, has several layers of various design and function, which can be changed without disturbing the layers already integrated with a newly created tissue.

In its most advanced example of execution the dressing consists of the active polymer layer including cells (fibroblasts and/or keratinocytes), which are additionally surrounded by a solution ensuring their survival. While causing no immunisation it provides an option for autologous as well as for allogeneic grafts i.e., of cells either from a patient or from unrelated donors. Those cells are a source of signals stimulating patient's tissues to regenerate, and they also can become a part of reconstructed patient's tissues, as it is in case of dressings of a design allowing a very large number of cells, exceeding 1 000 000 per $cm^2$.

Dressings using a similar phenomenon are known, such as Apligraf (U.S. Pat. Nos. 4,485,096; 5,106,949; 5,536,656). However, in their case cells are placed in gel, making communication with patient's tissues difficult, and significant positive polymer influence is lacking. Combination of cells with a polymer containing chitin derivatives results in unexpected synergistic influence on an affected tissue.

The dressing comprising the active polymer layer based on selected chitin derivatives is a new-generation dressing, belonging to active dressings. Advantageous features of such dressing are as follows:

maintaining appropriate healing environment (optimum humidity, constant temperature, slightly acidic pH range, correct gas exchange—optimum $pO_2$ and $pCO_2$ values), stimulation of migration of cells in inflammation and proliferation phases, stimulation of healing processes, absorption of intercapillary exudation, stimulation of fibroblasts, keratinocytes and granulation cells proliferation, stimulation of angiogenesis, protective functions (protecting a wound against contamination, irritation, mechanical damage, protection of newly created tissues at the stages of granulation tissue formation and epithelisation, protecting against skin maceration), perfect attachment to the place of application, need to remove used dressing is eliminated (enzymatic degradation of a dressing on a wound); when necessary, new dressings are applied on a previous dressing, no toxic and allergic effects.

The active polymer layer in accordance with the invention may also contain antibiotics and metronidazole bound to the polymer. Having antiprotozoal properties and antibacterial effect on anaerobic bacteria, metronidazole is one of the most effective chemotherapeutics for treatment of patients with infected wounds. The studies have showed that when administered orally, this medicine accelerates healing of second grade burns. Furthermore, metronidazole can protect patients against negative effects of oxidative stress induced by body burns. Moreover, the studies show that local application of metronidazole in treatment of vascular crural ulcerations may accelerate both granulation and epithelisation of the tissue [Witkowski J. A., Parish L. C.: *Pharmacol. and Therap.* 30, 1991, 660-1].

The dressing comprising the active polymer layer in accordance with the invention can be one-layered and fully biodegradable. The active polymer layer can be made of one chitin derivative (in the share of 0.1 to 100%) or a mixture of chitin derivatives (two or more chitin derivatives or chitin derivatives bounded with other commonly available biocompatible biodegradable polymers, such as for example: polilactide, polyglycol, polyesters of 3-hydroxybutyric acid and others) or is a biocomposite based on one or more chitin derivatives. In this case, the chitin derivative means chitin acylated with hydroxyacids (such as: lactic acid, glycolic acid), aliphatic anhydrides of a straight saturated chain (the length of the chain of acid radical C2 to C8 e.g. that is from acetic anhydride to octane anhydride and from anhydrides, such as: acetic-propionic anhydride, butanoic-propionic anhydride), aliphatic branched unsaturated anhydrides (e.g. methacrylic anhydride, 2-butenoic anhydride) or cyclic anhydrides (maleic anhydride, glutaric anhydride, succinic anhydride, phthalic anhydride). Chitin can be substituted in one or two positions by means of one or two substituents of different chain lengths. The active polymer layer has a three-dimensional structure (with pores of 0.1 mm to 4.0 mm in diameter, straight or coiled, depending on a wound type, or pores of a various size, percentage ratio of pores in a single dressing ranging from 1-90%).

The dressing comprising the active polymer layer in accordance with the invention can also contain an absorbent layer. The absorbent layer can be made of the following chemical compounds: hydrofibre, alginates, membranes and semi-permeable polyurethane films, hydrocolloids in form of plates, hydrocolloids in form of gel. Characteristics of individual absorbent layers:

- membranes and semi-permeable polyurethane films: polyurethane content from 15-100%, layer thickness from 0.1 mm-5.0 mm, shape and size depending on the internal layer. The external layer forming a barrier for microorganisms and water (waterproof), allowing, however, evaporation from wound surface, ensuring humid wound environment, easy to remove from the internal layer directly in contact with the wound. The absorbing layer of this type is designated for mildly and moderately exudating wounds.
- hydrofibre layer—based on carboxymethylocellulose (or other cellulose derivatives of similar physical and chemical properties), cellulose derivative content from 5-100%, layer thickness from 0.1 mm-5.0 mm, shape and size depending on the internal layer, in form of hydrophilic fibres compressed to form a plate. Fibres in contact with wound exudation form a gel coating—exudation is absorbed and captured in the fibre structure, thus eliminating pathogenic bacteria. Particularly recommended for neglected wounds, with large exudation and at risk of infection. Addition of silver ions (0.1-2%) provides this layer with antiseptic properties.
- alginate based layer—calcium and sodium-calcium alginates, obtained from sodium-calcium derivatives of alginic acid (D-mannuronic acid and L-glucuronic acid) and a polymer derived from sea brown algae (GG, MM, MG blocks; L-glucuronic acid 25-85%, mannuronic acid 20-70%, with a percentage content of glucuronic acid exceeding the mannuronic acid content; calcium ions content 0.1-10.0%, sodium ions content 0.1-2.0%). It is in form of a plate made of a net of compressed fibres. When wound exudation is absorbed, exudation-binding gel is formed around each fibre. The gelling phenomenon is based on exchange of calcium ions on fibre surface with sodium ions in exudation. The absorbing layer of this type is designated for moderately and strongly exudating wounds.
- hydrocolloid layer—in form of plates; the external protective layer is semipermeable (aim: protection against contamination and invasion of pathogenic microorganisms), the inner layer contains hydrophilic molecules of carboxymethylocellulose (sodium carboxymethylocellulose and other types of carboxymethylocellulose) suspended in hydrophobic pectin—ensuring appropriate humidity—and gelatine—ensuring slightly acidic pH-mixture. In contact with wound exudate it swells and, due to increasing molecule interactions, transforms into gel. A system of viscous colloids, congealing into a homogenous mass, is formed, in which free spaces are filled with absorbed exudate. That layer ensures maintenance of a very humid wound environment, constant temperature and slightly acidic pH range (reduces pain, acidic pH reduces $PGE_2$ prostaglandin production sensitising nerve endings). The absorbing layer of this type is designated for mildly and moderately exudating wounds.

The dressing comprising the active polymer layer in accordance with the invention can occur as a hydrogel with suspended molecules of chitin derivatives or their mixture. It stores a large amount of water (5-85%). Due to possible hydrophilic properties it ensures intensive moistening and hydration of a dry wound. It absorbs and binds wound exudation only to a small extent. It is designated for non-exudating wounds.

A dressing of this type is recommended for second-grade burns, abrasions and for covering of areas from which skin grafts were collected.

The usable form of a hydrogel dressing with suspended molecules of chitin derivatives or their mixtures is a flexible hydrogel panel of any shape and 3 to 6 mm in thickness. The dressing of this type is an effective barrier for a wound against the external environment, while it is permeable to oxygen and medicines.

The dressing comprising the active polymer layer in accordance with the invention can be made as gel. For this purpose a chitin derivative or a mixture of chitin derivatives and LiCl (5-6%)/N,N-dimethylacetamide (DMAC) system are used. Pores are obtained physically by aeration or chemically (using a reaction of 0.1-5% $CaCO_3$ with 1N HCl, resulting in $CO_2$ formation at 28-80° C.). The pores of a different course and 100-1000 μm are obtained. Both the pore size, and porosity (5-85%) are directly related to the size of calcium carbonate crystals (desirable size of grains is obtained with appropriate sieves with selected mesh size, 20-1000 μm) and their concentration (0.1-80%).

The usable form of a hydrogel dressing based on chitin derivatives is a flexible hydrogel panel of any shape and 2 to 8 mm in thickness. The dressing of this type is an effective barrier protecting a wound against the external environment, while it is permeable to oxygen and medicines.

The dressing comprising the active polymer layer in accordance with the invention can contain a layer of fibroblasts and/or keratinocytes. Fibroblasts will form autologous or allogeneic graft, of cells either from a person receiving the dressing or from related or unrelated donors. The number of cells should range from 10 000 to 1000000 per square centimetre of the dressing surface, and depends on a number and a size of pores formed in the polymer. The number of cells increases with the volume of created spaces.

The dressing of that type can be of any shape, adjusted to individual needs of a patient (circular, square, rectangular, tapes, anatomic shapes, etc.). Thickness of a single dressing can range from 0.1 mm to 5.0 mm.

The technical parameters characterising a single-layer dressing, depending on the polymer layer thickness and chitin derivatives used:
  oxygen permeability ($cm^3/m^2$)—500-9000
  elongation—0.5-500%
  tensile strength ($kg/cm^2$)—1-200
  PBS absorbance (0.2-50 g PBS/24 h/100 $cm^2$ of a dressing).

The application of the dressings comprising the active polymer layer in accordance with the invention: crural ulceration, pressure ulceration, diabetic gangrene, abscesses, boils, carbuncles, burns, dressing of wounds in traumatology and neoplastic surgery, and other. When there are necrotic tissues in the wound, it is recommended to apply ointment containing proteolytic enzymes (before a dressing based on chitin derivatives is applied) or other medication for autolytic cleaning of necrotic tissues in the wound, or to clean the wound surgically.

In the biological studies, conducted in vitro and in vivo on fibres and non-fibrous of dibutyryl chitin (DBC), no allergic reactions, and no increase in the tissue reaction following their intraperitoneal implantation confirmed that DBC meets basic biological requirements for medical devices, specified in the standard PrPN-EN 10993 "Biological evaluation of medical devices". Results of those studies were published [A. Chilarski, L. Szosland, I. Krucińska, P. Kiekens, A. Błasińska, G. Schoukens, R. Cisło, J. Szumilewicz, "*Fibres &Textiles in Eastern Europe,* 2007, Vol. IV, str. 77-81].

In the clinical studies conducted at the Paediatric Surgery and Urology Clinic of the Polish Mothers Memorial Hospital and Research Institute in Lodz, in the years 2003-2005, a spontaneous effect of DBC was demonstrated, as a factor accelerating healing of numerous types of wounds. Chitin derivatives formed into non-fibrous were also previously tested under the European project CHITOMED (Biomedical Textiles from Dibutyrylchitin and Chitin), at the laboratories of the Lodz University of Technology and Universiteit Gent (Belgium) and during the clinical studies at the Paediatric Surgery and Urology Clinic of the Polish Mothers Memorial Hospital and Research Institute in Lodz managed by Professor Andrzej Chilarski.

The dressing comprising the active layer polymer according to the invention is shown in the drawing, wherein.

EXAMPLE 1

Single-Layer Dressing Comprising the Active Polymer Layer 1, Fully Biodegradable The dressing consists of one layer. The active polymer layer 1 is produced of one chitin derivative obtained w by the esterification reaction with propionic anhydride (percentage concentration of chitin derivative in the dressing is 100%). A dissolved derivative chitin in the concentration of 10-30% in acetone is poured out by a nozzle of a diameter of 2-8 mm with a speed of 1-3 l/min on the flat non-absorbing surface (form of tape) of a width of 100 mm with a constant transport of 0.5-1.0 meters per minute. Once the polymer tape is solidified it is possible to make holes with a prepared stamp (needles size from 0.098 to 3.98 mm) with a different courses, sizes and density of arrangement and shaping thus obtained polymer tape to shape depending on the type and destination of the dressing. As a result of this process an active polymer layer is produced. It has a three-dimensional porous structure or non-porous structure (in case of porous structure—pores of 0.1 mm to 4.0 mm in diameter, straight or coiled, or pores of mixed size, pores percentage ratio in a single dressing from 1-90%). The active polymer layer 1 was additionally saturated with excipients or other antiseptic substances by immersing ready active polymer layer 1 in the solution of excipient and then adsorption from the solution by evaporating of the solvent. Active polymer layer was saturated with excipients such as: $Ag^+$ ions in the amount of 0.01%, $Ca^{2+}$ ions in the amount of 0.01%. The active polymer layer 1 was also saturated with neomycin, an antibiotic with antiseptic and bacteriostatic properties.

Eventually, the active polymer layer 1 comes into contact directly with the wound.

Technical Parameters Characterising the Single-layer Dressing Depending on the Active Polymer Layer Thickness and Porosity:

oxygen permeability ($cm^3/m^2$)—1000-9000,
elongation—0.5-400%,
tensile strength ($kg/cm^2$)—1-200,
PBS absorption (0.2-50 g PBS/24 h/100 $cm^2$ of the dressing)

EXAMPLE 2

Single-layer Dressing Comprising the Active Polymer Layer 1 Fully Biodegradable The dressing consists of one layer. The active polymer layer 1 was produced of the mixture of three chitin derivatives (acetic derivative 10%, pentanoic derivatives 10% and butanoic derivatives 80%). Dissolved polymer mixture with the addition of excipients (mentioned below) in the concentration of 5-30% in ethanol is poured out by a nozzle of a diameter of 2-8 mm with a speed of 0.5-3.0 l/min on the flat non-absorbing surface (form of tape) of a width of 100 mm with a constant transport of 0.5-1.0 meters per minute. Next, after solidification of poured out layers, the active polymer layer 1 is formed. The obtained active layer polymer is formed to shape depending on the type and destination of the dressing. The active polymer layer 1 was saturated with excipients such as $K^+$ ions, citric acid in the amount of 1.5%, bismuth salts in the amount of 0.001%. The active polymer layer 1 was also saturated with antibiotic vancomycin (0.1%).

Figure 1:
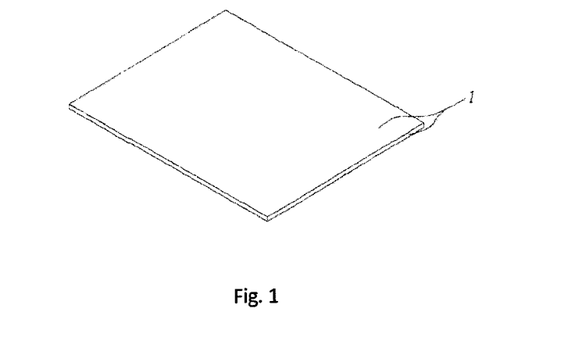
FIG. 1 shows the single-layer dressing fully biodegradable comprising the active layer based on the chitin derivatives.

Eventually, active polymer layer 1 comes into contact directly with the wound, it has three-dimensional porous structure as presented in the FIG. 1.

Technical Parameters Characterising the Single-layer Dressing Depending on the Active Polymer Layer Thickness and Chitin Derivatives used:
- oxygen permeability ($cm^3/m^2$)—500-3000,
- elongation—0.5-500%,
- tensile strength ($kg/cm^2$)—1-200,
- PBS absorption (0.2-50 g PBS/24 h/100 cm2 of the dressing)

Application method: Delicately apply a single-layer biodegradable dressing on a previously cleaned wound and press. The active polymer layer 1 based on chitin derivatives is not removed from the wound but left for enzymatic biodegradation, the rate of which depends on a wound type, as well as on thickness of the dressing.

EXAMPLE 3

Two-layer Dressing Comprising the Active Polymer Layer 1 Fully Biodegradable The dressing consists of two layers. First (outer) one is removable protective film 2, and the second (the active polymer layer 1) consists of a mixture of three chitin derivatives (acetate 10%, pentane 20% and butane 20% derivatives) bound to biocompatible biodegradable polymers—polylactatide, 30%, and polyester of 3-hydroxybutyric acid, 20%. Active polymer layer 1 prepared according to the description of example 1. The outer layer and the active polymer layer are bound by a peripheral adhesive system 2 in form of acrylic adhesive, both layers are sealed with their side edges (0.1-10% of adhesive on a dressing surface) as presented in the FIG. 2. Active polymer layer 1 additionally was saturated with the excipients and bactericidal substances by immersing ready active layer in the solution of an active substance and then adsorption from the solution by evaporating of the solvent. Active polymer layer 1 comprises $Ag^+$ ions in the amount of 2.0%, $Zn^{2+}$ ions in the amount of 0.1%, citric acid in the amount of 0.3%. The active polymer layer 1 was also saturated with an antibiotic: gentamycin (0.1%).

Figure 2:
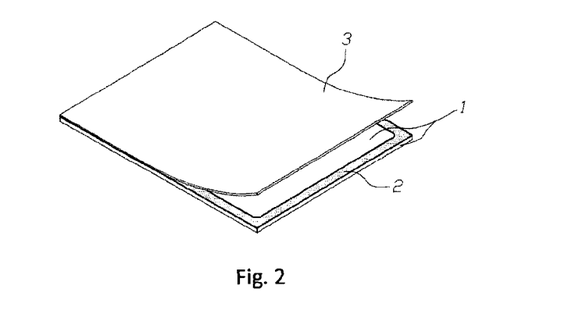
FIG. 2 shows the two-layer dressing fully biodegradable.

Technical Parameters Characterising the Two-layer Wound Dressing, Depending on the Active Polymer Layer 1 Thickness and Chitin Derivatives Used:
- oxygen permeability ($cm^3/m^2$)—500-9000,
- elongation—0.5-500%,
- tensile strength ($kg/cm^2$)—1-200,
- PBS absorption (0.2-50 g PBS/24 h/100 cm2 of the dressing);

Application method: Delicately apply a two-layer biodegradable dressing on a previously cleaned wound and press, and after predetermined time remove the protective outer layer 3. Only the active polymer layer 1 is left on the wound. The active polymer layer 1 is not removed from the wound but left for enzymatic biodegradation, the rate of which depends on a wound type, as well as on thickness and porosity of the dressing.

EXAMPLE 4

Three-layer Dressing Comprising the Active Polymer Layer 1, Fully Biodegradable Three-layer dressings are highly absorbent dressings in which the absorbent layer ensures optimal humid environment of the wound, at the same time preventing accumulation of the exudate in the wound and preventing maceration of healthy skin around it.

Figure 3:
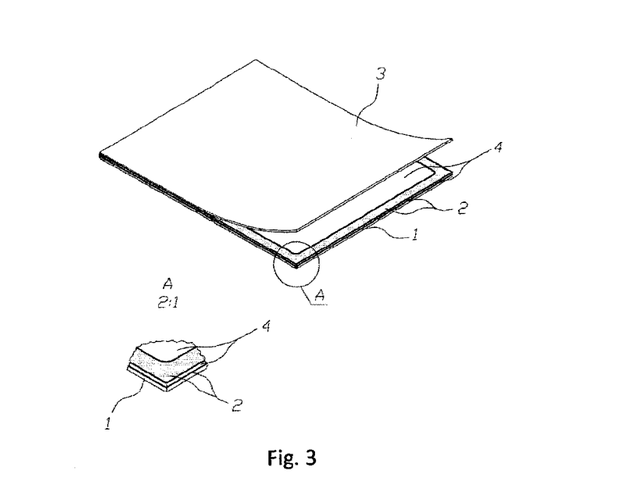
FIG. 3 shows the three-layer dressing fully biodegradable.

The dressing consists of three layers. The outer one is removable protective imperforated film 3. The inner layer is absorbent layer 4, which is arranged between the outer layer and the active polymer layer 1. The active polymer layer 1 is made of a mixture of three chitin derivatives (obtained by an esterification reaction of chitin with the following anhydrides successively: acetate-propane, 20%, butane-propane 40% and methacrylic 20%), combine with widely available biocompatible biodegradable polymer polyglycol (polyglycol percentage was 20%).

The active polymer layer 1 was made and saturated with excipients according to the description of the example 1. The active polymer layer 1 was saturated with $Ag^+$ ions in the amount of 2.5%, $K^+$ ions in the amount of 0.1%, bismuth salts in the amount of 0.1%. The active polymer layer 1 was also saturated with metronidazole (0.3%).

The absorbent layer 4 is bound to the outer layer 3 and the active polymer layer 1 by a peripheral adhesive system 2 (polyvinyl adhesive). All three layers are sealed with their side edges (0.1-10% of adhesive on a dressing surface). The absorbent layer 4 is made of commercial available hydrofibres (FIG. 3).

Technical Parameters Characterising the Three-layer Wound Dressing, Depending the Thickness and Porosity of the Active Polymer Layer 1:
- oxygen permeability ($cm^3/m^2$)—200-9000,
- elongation—0.5-500%,
- tensile strength ($kg/cm^2$)—1-300,
- PBS absorption (0.2-70 g PBS/24 h/100 $cm^2$ of the dressing);

Application method: Delicately apply a three-layer biodegradable dressing on a previously cleaned wound and press. When the absorbent layer 4 is saturated (visible increase in the absorbent layer 4 volume; depending on the wound type and quantity of exudates, the time ranges from 5 to 168 hours), the absorbent layer 4 with the outer layer 3 should be delicately removed from the active polymer layer 1, which is left for enzymatic biodegradation, the rate of which depends on a wound type, as well as on thickness and porosity of the layer.

EXAMPLE 5

Three-layer Dressing Comprising the Active Polymer Layer 1, Fully Biodegradable Three-layer dressings are highly absorbent dressings in which the absorbent layer 4 ensures optimal humid environment of the wound, at the same time preventing accumulation of the exudate in the wound and preventing maceration of healthy skin around it.

The dressing consists of three layers. The outer one is removable protective imperforated film 3. The inner layer is absorbent layer 4, which is arranged between the outer layer and the active polymer layer 1. The active polymer layer 1 is made of a mixture of three chitin derivatives (obtained by an esterification reaction of chitin with the following anhydrides successively: acetate-propane, 20%, succinate 40% and phthalate 20%), combine with widely available biocompatible biodegradable polymer polyglycol (polyglycol percentage was 20%). The active polymer layer 1 was made and saturated with excipients according to the description of the example 1. The active polymer layer 1 was saturated with $Ag^+$ ions in the amount of 2.5%, $Ca^{2+}$ ions in the amount of 1.0%, $Zn^{2+}$ ions in the amount of 0.1%. The active polymer layer 1 was also saturated with metronidazole (0.3%).

The absorbent layer 4 is bound to the outer layer 3 and the active polymer layer 1 by a peripheral adhesive system 2 (polyvinyl adhesive). All three layers are sealed with their side edges (0.1-10% of adhesive on a dressing surface). The absorbent layer 4 is made of alginates (FIG. 3).

Technical Parameters Characterising the Three-layer Wound Dressing, Depending the Thickness and Porosity of the Active Polymer Layer:
- oxygen permeability ($cm^3/m^2$)—200-9000,
- elongation—0.5-500%,
- tensile strength ($kg/cm^2$)—1-300,
- PBS absorption (0.2-70 g PBS/24 h/100 $cm^2$ of the dressing);

Application method: Delicately apply a three-layer biodegradable dressing on a previously cleaned wound and press. When the absorbent layer 4 is saturated (visible increase in the absorbent layer 4 volume; depending on the wound type and quantity of exudates, the time ranges from 5 to 168 hours), the absorbent layer 4 with the outer layer 3 should be delicately removed from the active polymer layer 1, which is left for enzymatic biodegradation, the rate of which depends on a wound type, as well as on thickness and porosity of the layer.

EXAMPLE 6

Figure 4:
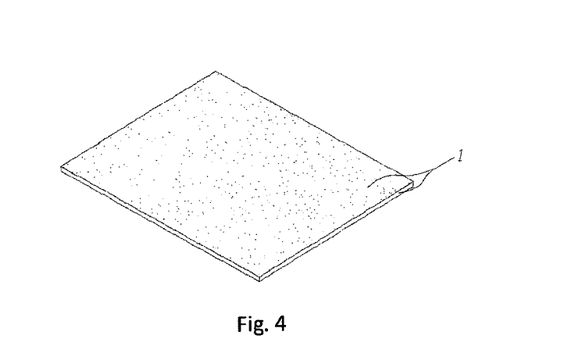
FIG. 4 shows the single-layer dressing fully biodegradable made by leaching method.

Single-layer Dressing Comprising the Active Polymer Layer 1 Fully Biodegradable, Made with the Leaching Method The polymer porous dressing of three-dimensional structure is based on a mixture of chitin derivatives obtained with propane 20%, acetate, 30%, and 2-butene, 50%, anhydrides. Pores are made by leaching. In the method, a mould (of a shape depending on the final shape of the dressing) NaCl, with crystals of a size (from 100 to 800 µm), is spread evenly (polymer weight/porogenic substance weight is 1/5 to 1/40), and then the polymer acetone solution is applied delicately; the polymer mixture concentration in the solvent is 0.02 g/ml. Then the solvent was evaporated at 24° C. for 2 hours. The porogenic substance and solvent residues are washed out with water, (possibly) deionised, for 1-24 h. After complete washing out of the porogenic substance a porous active polymer layer 1 of three-dimensional structure and porosity ranging from 5 to 99% per the dressing surface is formed. The size of obtained pores ranges from 50 to 600 µm (FIG. 4).

The active polymer layer 1 was saturated with excipients of bactericidal characteristic by immersing ready active polymer layer 1 in the solution of excipient and then adsorption from the solution by evaporating of the solvent. The active polymer layer 1 contained $Ag^+$ ions in the amount of 0.2%, citric acid in the amount of 0.003%. The active polymer layer 1 was also saturated with an antibiotic: vancomycin (0.5%).

A dressing of this type is not removed from the wound but left for enzymatic biodegradation, the rate of which depends on a wound type, as well as on porosity of the active polymer layer 1.

Technical Parameters Characterising the Single-layer Dressing, Depending on Thickness and Porosity of the Polymer Layer:
- oxygen permeability ($cm^3/m^2$)—200-9000,
- elongation—0.5-35%,
- tensile strength ($kg/cm^2$)—1-200,
- PBS absorption (0.2-30 g PBS/24 h/100 $cm^2$ of the dressing);

Application method: Delicately apply a single-layer biodegradable dressing on a previously cleaned wound and press. A dressing of this type is not removed from the wound but left for enzymatic biodegradation, the rate of which depends on a wound type, as well as on thickness and porosity of the dressing. When necessary, on a degraded dressing another dressing of this type is applied, without removing the previous one.

EXAMPLE 7

Two-layer Wound Dressing, Fully Biodegradable Made with the Leaching Method

Figure 5:
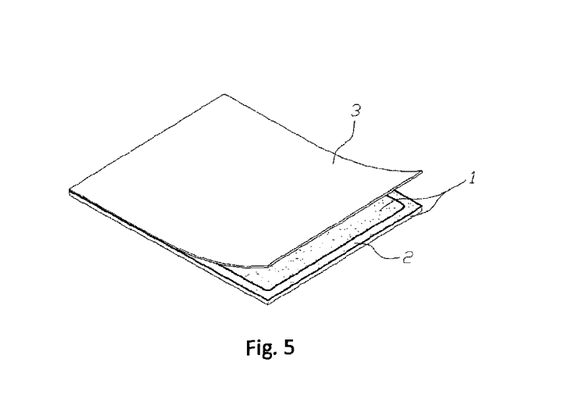
FIG. 5 shows the two-layer dressing fully biodegradable made by leaching method.

The dressing consists of two layers. The first (outer) one is removable protective film 3 (commercially available, perforated or imperforated), while the second (active) layer is an active polymer porous layer 1 of three-dimensional structure, based on a mixture of chitin derivatives obtained with butane, 80%, and acetate, 20%, anhydrides. Pores are made by leaching. In a mould (of a shape depending on the final shape of the dressing) NaCl, with crystals of a size (from 100 to 800 µm), is spread evenly (polymer weight/porogenic substance weight is 1/5 to 1/40), and then the polymer ethanol solution is applied delicately; the polymer mixture concentration in the solvent is 0.03 g/ml. The solvent is evaporated at 30° C. and reduced pressure, for ca. 3 hours. The porogenic substance and solvent residues are washed out with water, (possibly) deionised, for 1-24 h. After complete washing out of the porogenic substance an active porous polymer dressing of three-dimensional structure and porosity ranging from 5 to 99% per the dressing surface is formed. The size of obtained pores ranges from 50 to 600 µm (FIG. 5).

Active polymer layer 1 additionally was saturated with excipients with bactericidal properties by immersing ready active layer in the solution of excipient and then adsorption from the solution by evaporating of the solvent. Active polymer layer 1 contained $Ag^+$ ions in the amount of 1.5%, $Zn^{2+}$ 0.01%, citric acid in the amount of 3.1%. The active polymer layer 1 was also saturated with an antibiotic: cephalosporin (0.1%).

Technical Parameters Characterising the Two-layer Wound Dressing, Depending on Porosity of the Active Polymer Layer:
- oxygen permeability ($cm^3/m^2$)—200-9000,
- elongation—0.5-35%,
- tensile strength ($kg/cm^2$)—1-200,
- PBS absorption (0.2-30 g PBS/24 h/100 cm2 of the dressing);

Application method: Delicately apply a two-layer biodegradable dressing on a previously cleaned wound and press, and after predetermined time remove the protective film 3. The active polymer layer 1 is not removed from the wound but left for enzymatic biodegradation, the rate of which depends on a wound type, as well as on thickness and porosity of the layer. When necessary, on a degraded dressing another dressing of this type is applied, without removing the previous one.

EXAMPLE 8

Figure 6:
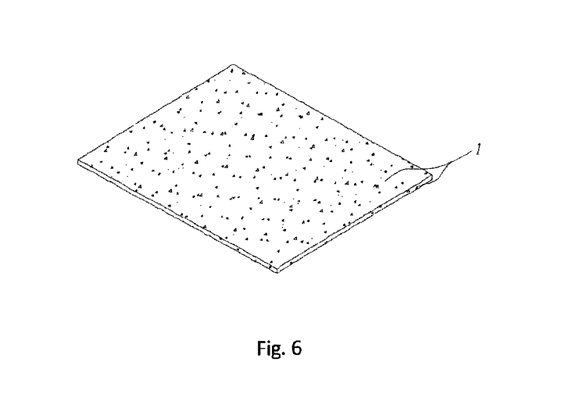
FIG. 6 shows the hydrogel dressing with suspended particles of chitin derivatives or their mixtures.

Hydrogel Dressing Comprising the Active Polymer Layer 1 with Suspended Molecules of Chitin Derivatives or their Mixtures A porous dressing of this type is formed by a three-dimensional gelatine mesh, comprises the active polymer layer 1 as interspersed molecules of chitin derivatives obtained with maleic, 60%, and glutaric, 40%, anhydrides (0.01-98% w/w of a chitin derivatives mixture per gel volume). To previously prepared aqueous gelatine solution with the addition of excipients with a bactericidal properties (5% gelatine solution in water, the temperature of the sol homogenization 40° C.) added 5% mixture of chitin derivatives and it was mixed at 40° C. for 2 h using a magnetic stirrer of a rotary speed of 1200 revolutions per minute. Next, gelatine with suspended particles of chitin derivatives mixture was applied on non-absorbing surface (form of tape) of a width of 100 mm with a speed of 0.25-3 l/min by means of nozzle of a diameter of 0.2-10 mm with a speed of transport of 0.3-1.0 meters per minute and cooled to temp. 30° C. Next, obtained gel layer was formed to the destined shape dependent on the type and destination of the dressing. It stores significant amount of water (5-85%). Due to possible hydrophilic properties it ensures intensive moistening and hydration of a dry wound. It absorbs and binds wound exudation only to a small extent. It is designated for non-exudating wounds. The gel layer is saturated with excipients as described in the example 1 such as $Ag^+$ ions in the amount of 2.5%, $K^+$ ions in the amount of 0.1%, $Ca^{2+}$ in the amount of 1.2%. The hydrogel layer was also saturated with an antibiotic: polymyxin B (0.2%).

A dressing of this type is recommended for second-grade burns, abrasions and for covering of areas from which skin grafts were collected.

The usable form of a hydrogel dressing with suspended molecules of chitin derivatives is a flexible hydrogel panel of any shape and 3 to 6 mm in thickness. The dressing of this type is an effective barrier for a wound against the external environment, while it is permeable to oxygen and medicines (FIG. 6).

Technical Parameters Characterising the Hydrogel Dressing with Suspended Molecules of Chitin Derivatives, Depending on the Dressing Thickness:

oxygen permeability ($cm^3/m^2$)—100-500,
    elongation—0.5-60%,
    tensile strength ($kg/cm^2$)—1-100,
    PBS absorption (0.2-20 g PBS/24 h/100 $cm^2$ of the dressing);

Application method: Contrary to previous examples (Examples from 1 to 7), a dressing of this type should be removed from a wound after the specified time (5-168 h, depending on the wound healing stage), however, that stage is painless for the patient, as this type of the dressing does not adhere excessively to a wound.

EXAMPLE 9

Hydrogel Dressing Comprising the Active Polymer Layer 1 with Suspended Molecules of Chitin Derivatives or their Mixtures A non-porous dressing formed by the three-dimensional ethylene polyglycol mesh, comprises the active polymer layer 1 as interspersed molecules of chitin derivatives obtained with maleic, 60%, and glutaric 40% anhydrides (0.01-98% w/w of a chitin derivatives mixture of gel volume). To previously prepared polyglycol ethylene sol with the addition of excipients with bactericidal properties added 8% mixture of chitin derivatives and mixed at the room temperature for 2 h using a magnetic stirrer of a rotary speed of 1200 per minute. Next, sol with suspended particles of chitin derivatives mixture was applied on non-absorbing surface (form of tape) of a width of 100 mm with a speed of 0.25-3 l/min by means of nozzle of a diameter of 2-10 mm with a speed of transport of 0.3-1.0 meters per minute and subjected to gelation. Next, the gel layer was formed to shape depending on the type and destination of the dressing. The dressing based on such combination of chitin derivatives and this type of hydrogel accumulates substantial amount of water (5-70%). Moreover due to possible hydrophilic properties it ensures intensive moistening and hydration of a dry wound. It absorbs and binds wound exudation only to a small extent. It is designated for non-exudating wounds. The hydrogel layer with applied the active polymer layer 1 on, was saturated with the excipients as described in the example 1. It contained $Ag^+$ ions in the amount of 0.02%, citric acid in the amount of 0.03%, bismuth salts in the amount of 0.01%. The hydrogel layer was also saturated with an antibiotic: polymyxin B (0.3%) (FIG. 6).

Technical parameters as in the example 8.

Application method as for the dressing obtained in the example 8.

EXAMPLE 10

Figure 7:
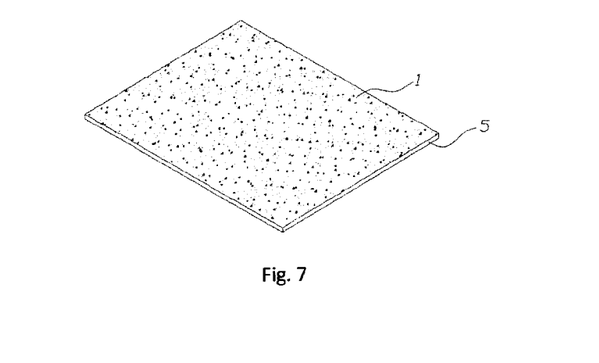
FIG. 7 shows the hydrogel dressing with the particles of chitin derivatives or their mixtures on the surface of dressing.

Hydrogel Dressing Comprising the Active Polymer Layer 1 with Molecules of Chitin Derivatives or their Mixtures on the Dressing Surface A hydrogel dressing covered on one side with the active polymer layer 1 in the form of molecules of chitin derivatives or their mixtures. A dressing formed by the three-dimensional hydrogel mesh 5 based on polyacrylic acids, with the addition of excipients with a bactericidal properties, covered on the side being in direct contact with a wound by a layer of a mixture of chitin derivatives (0.01-1.5 mm) thick. The mixture of chitin derivatives was obtained with hexane, 20% and heptane, 80%, anhydrides (0.01-98% w/w of a chitin derivatives mixture per gel volume).

Previously prepared sol based on polyacrylic acids was applied on non-absorbent surface (form of tape) of a width of 100 mm with a speed of 0.25-3 l/min by means of nozzle of a diameter of 2-10 mm with a constant speed of transport of 0.2-1.0 meters per minute, and then poured out sol was dusted by a milled mixture of polymers of a graining of 100-350 μm. Resulting system was subjected to gelation (FIG. 7) and then formed into the shape dependent on the type and destination of the dressing.

Technical Parameters Characterising the Hydrogel Dressing with Molecules of the Mixture of the Chitin Derivatives on the Dressing Surface, Depending on Percentage Content of Chitin Derivatives and Dressing Thickness:

oxygen permeability ($cm^3/m^2$)—100-500,
    elongation—0.5-60%,
    tensile strength ($kg/cm^2$)—1-100, Application method: Contrary to previous examples (Examples from 1 to 7), a dressing of this type should be removed from a wound after the specified time (5-168 h, depending on the wound healing stage), however, that stage is painless for the patient, as this dressing does not adhere excessively to a wound.

EXAMPLE 11

Hydrogel Dressing Comprising the Active Polymer Layer 1 with Molecules of Chitin Derivatives or their Mixtures on the Dressing Surface A hydrogel dressing covered on one side with the active polymer layer 1 in the form of molecules of chitin derivatives or their mixtures. A dressing formed by the three-dimensional hydrogel mesh 5 based on agar mesh, covered on the side being in direct contact with a wound by an active polymer layer 1 (0.01-1.5 mm) thick, of a mixture of chitin derivatives obtained with octane, 20% and heptane, 80%, anhydrides (0.01-98% w/w of a chitin derivatives mixture per gel volume) (FIG. 7).

A method of the dress preparation as in the example 10.

Technical parameters as in the example 10.

Application method as for the dressing obtained in the example 10.

EXAMPLE 12

Figure 8:
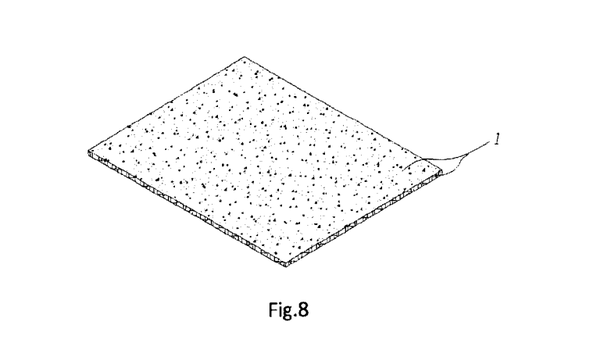
FIG. 8 shows the gel dressing of a porous structure based on chitin derivatives.

Porous Gel Dressing Comprising the Active Polymer Layer 1 Based on Chitin Derivatives A gel dressing comprising the active polymer layer 1 formed with a mixture of chitin derivatives obtained with acetic, 30%, and propane, 70%, anhydrides, and on the LiCl (5-6%)/DMAc system. Pores are obtained chemically with a chemical method (using 2% $CaCO_3$ reaction with 1N HCl, resulting in formation of $CO_2$ at 28° C.). The pores of the size of 100-1000 μm are obtained. Both, the size of the pores and the porosity (5-85%) are directly related to the size of calcium carbonate crystals (desired grain size is obtained by using appropriate sieves of selected porosity 20-1000 μm) and its concentration (0.1-80%).

A method of preparing the active polymer gel layer 1: to previous prepared solution of LiCl (5-6%)/DMAC added 2% mixture of chitin derivatives (the composition of the mixture is described above). Next, the solution was mixed using a magnetic stirrer of a speed of 1500 revolutions per minute at 8° C. for 24 h. To prepared solution added of calcium carbonate 2% and mixed at reduced temperature using the same parameters of revolutions for another 3 h. Next, the solution was poured on non-absorbing surface (form of tape) of a width of 100 mm with a speed of 0.25-3 l/min by means of nozzle of a diameter of 2-10 mm with a speed of transport of 0.2-1.0 meters per minute. Then, the solution was left to evaporate of the solvent for 48 h. The pores was obtained by multiple washing using 1 N HCl at 28° C. The trace residues of lithium chloride and of the solvent were removed by multiple extractions with water. Last step was drying the resulting active porous polymer gel layer 1, possibly at reduced temperature −40° C. (FIG. 8). Technical Parameters Characterising the Porous Gel Dressing Comprising the Active Polymer Layer 1 Depending on Percentage Content of Chitin Derivatives and Dressing Thickness:

oxygen permeability ($cm^3/m^2$)—100-8000, elongation—0.5-40%, tensile strength ($kg/cm^2$)—1-200, PBS absorption (0.2-10 g PBS/24 h/100 $cm^2$ of the dressing);

Application method: Contrary to previous examples (Examples from 1 to 7), a dressing of this type should be removed from a wound after the specified time (5-168 h, depending on the wound healing stage), however, that stage is painless for the patient, as this type of the dressing does not adhere excessively to a wound.

EXAMPLE 13

Porous Gel Dressing Comprising the Active Polymer Layer 1 Based on Chitin Derivatives A gel dressing comprising the active polymer layer 1_based on a mixture of chitin derivatives obtained with acetic, 30%, and propane, 70%, anhydrides, and on the LiCl (5%)/DMAc system. Pores are obtained chemically with a chemical method (using 3.5% $CaCO_3$ reaction with 1N HCl, resulting in formation of $CO_2$ at 28° C.). The pores of the size of 100-1000 μm are obtained. Both, the size of the pores and the porosity (5-85%) are directly related to the size of calcium carbonate crystals (desired grain size is obtained by using appropriate sieves of selected porosity 20-1000 μm) and its concentration (0.1-80%).

A method of preparing of the above dressing: to previous prepared solution of LiCl (5-%)/DMAC added 4% mixture of chitin derivatives (the composition of the mixture is described above). Next, the solution was mixed using a magnetic stirrer of a speed of 1500 revolutions per minute at 8° C. for 24 h. to prepared solution of added of calcium carbonate 3.5% and mixed at reduced temperature using the same parameters of revolutions for another 3 h. Next, the solution was poured on non-absorbing surface of a width of 100 mm by means of nozzle of a diameter of 2-10 mm with a speed of transport of 0.2-1.0 meters per minute. Then, the solution was left to evaporate of the solvent for 48 h. The pores was obtained by multiple washing using 1 N HCl at 28° C. The trace residues of lithium chloride and of the solvent were removed by multiple extractions with water. Last step was drying resulting the active polymer porous layer 1, possibly at reduced temperature −40° C. (FIG. 8).

Technical parameters as in the example 12.

Application method as for the dressing obtained in the example 12.

EXAMPLE 14

Porous Gel Dressing Comprising the Active Polymer Layer 1 Based on Chitin Derivatives A gel dressing comprising the active polymer layer 1_based on a mixture of chitin derivatives obtained with acetic, 30%, and propane, 70%, anhydrides, and on the LiCl (6%)/DMAc system. Porosity is obtained with a leaching method, in which sodium chloride is used as a porogenic substance. In the mould (the shape of the mould depends on the end shape of the dressing) in a uniform manner is placed NaCl (the weight of polymer/the weight of porogene is from 1/5 to 1/40), with crystals of sizes (100-800 μm), and then in a delicate way the solution of a mixture of chitin derivatives dissolved in a previously prepared LiCl/DMAc system is applied; wherein the concentration of the mixture of chitin derivatives in the solvent system is 0.03 g/ml. Evaporation of the solvent occurs at 30° C. for 48 h. The solvent and the porogenic substance are removed through extraction with water and repeatable rinsing with deionised water (up to 24 h). Then the active polymer layer 1 is dried possibly at a reduced temperature (−40° C.). Size of the pores may range from 50 to 500 μm. As a result of the process, the porous active polymer layer 1 of a three-dimensional structure and porosity from 5 to 99% on a surface of the dressing (FIG. 8) is obtained.

Technical parameters as in the example 12.

Application method as for the dressing obtained in the example 12.

EXAMPLE 15

Porous Gel Dressing Comprising the Active Polymer Layer 1 Based on Chitin Derivatives A gel dressing comprising the active polymer layer 1 based on a mixture of chitin derivatives obtained with acetic, 30%, and propane, 70%, anhydrides, and on the LiCl (6%)/DMAc system. Pores are obtained physically by aeration (FIG. 8).

Technical parameters as in the example 12.

Application method as for the dressing obtained in the example 12.

EXAMPLE 16

Single-layer Wound Dressing, Comprising the Active Polymer Layer 1, Fully Biodegradable Made with the Leaching Method, Enriched with Cells (Fibroblasts 7 and/or Keratinocytes 6)

Figure 9:
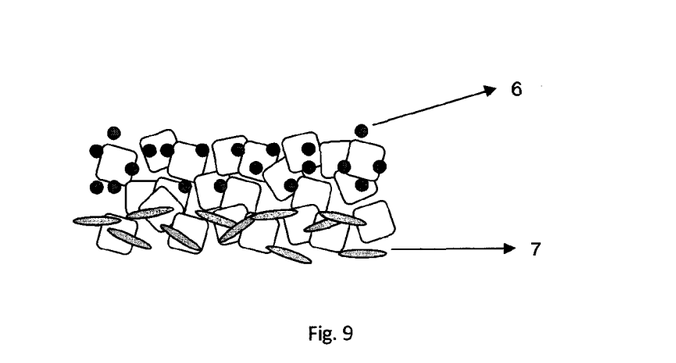
FIG. 9 shows the single-layer dressing fully biodegradable made by leaching method enriched with cells (fibroblasts and/or keratinocytes)

The active polymer layer 1 is formed in accordance with the example 4. After sterilisation of the active polymer layer 1 forming the dressing with ionising radiation, the dressings are immersed in a solution containing a growth medium for human fibroblasts 7 and/or keratinocytes 6, FIG. 9, together with the cells. The measure was performed by automatic counter of cells showing the ability to bonding of 80% placed on polymer cells in the range from 100 000 to 500 000 applied cells. The dressing prepared in this way, protected in a way preventing contamination with contaminants from the external environment, and maintained at the temperature of 4° C., can be transported to be applied to a patient. This combination allows significant stimulation of cell divisions in a patient due to the effect of the polymer, as well as of chemotactic factors in transplanted cells. The dressings containing the highest number of transplanted cells form a component of the patient's rebuilding tissue, in addition to being responsible for stimulation of his/her cells.

EXAMPLE 17

Single-layer Wound Dressing Comprising the Active Polymer Layer 1, Fully Biodegradable Made with the Leaching Method and a Procedure for Applying the Cells The active polymer layer 1 is formed in accordance with the example 4. After sterilisation of the active polymer layer 1 forming the dressing with a blast of overheated steam or ionising radiation, the dressings are immersed in a solution containing a growth medium for human fibroblasts 7. The dressing prepared in this way, protected in a way preventing contamination with contaminants from the external environment can be transported to be applied to a patient. Immediately before applying the dressing to an affected area a doctor conducting the procedures adds cells from a prepared container onto the dressing surface, previous applied to the wound of the dressing. This combination allows significant stimulation of cell divisions in a patient due to the effect of the polymer, as well as of chemotactic factors in transplanted cells. The dressings containing the highest number of transplanted cells form a component of the patient's rebuilding tissue, in addition to being responsible for stimulation of his/her cells.

Results of Comparative Currently Used Solutions

Comparative analysis for some exemplary embodiments according to the invention was performed, which showed better properties than dressings prepared on the base of unwoven fabric. The comparison was performed in conditions in vitro by means of generally accepted tests inter alia for evaluation of the healing process.

1. Test of Skinning Over

In the dish of a circular section were applied two dies of a half-moon shape and such selected size as after their placing, between them space zone and width of 7 mm was left. On the polymer layer limited with the described dies were applied 250 000 cells in the volume of 0.5 ml. After sedimentation of cells and their bounding with the substrate, the dies were removed. The time of skinning over of the empty surface between the occupied areas are presented in the table. The fastest time of skinning over is evidenced by the greatest potential medicinal.

2. The Estimation of a Viability after Culturing on the Selected Substrate/Functional Analysis The cells (500 000 in each culturing dish) on the substrate constructed from the tested polymers were cultivated for the period of 2 weeks. At this time, necessary replacements of culture medium every 2-3 days was performed, and also growth state was microscopic controlled. After this period the cells were treated with trypsin-EDTA (PAA) in order to their enzymatic release from the substrate (polymer), with which they bound during the growth. Next, the cells were applied to identical culture dishes and the density sedimented cells after 12 hours was evaluated. This test allows the functional evaluation of the cells state. The cells cultivated with the derivatives, in the appropriate for their growth conditions, have very high ability to adhesion and therapeutic action. The higher density of cells is evidence of maintaining of the most suitable conditions for growth and function of the cells.

3. Evaluation of Viability after Culturing on the Selected Substrate/Immunofluorescence Analysis The cells (500 000 in each in each culturing dish) on the substrate constructed from selected polymers were cultivated for the period of 1 week. At this time necessary replacements of culture medium was performed, and also growth state was microscopic controlled. After this period the cells were treated with trypsin-EDTA (PAA) in order to their enzymatic release from the substrate (polymer), with which they bound during the growth. Next, cells suspended in buffer PBS were applied on microscopic slide and mixed with fluorescein diacetate (dyeing living cells) and ethidium bromide (dyeing dead cells). These dyes are used in the tests of viability based on double dyeing, allowing for visualization simultaneously living and dead cells. After 3 minutes, in fluorescence microscope (in the blue-violet light) the cells luminous on the green (living) and luminous on the red (dead) were counted. The higher number of living cells indicates better growth properties of given polymer and its embodiment, which translates into higher therapeutic potential.

4. Adhesion Test of the Cells to the Surface of Polymer

The cells (500 000 in each culturing dish) on the substrate constructed from selected polymers were cultivated for the period of 3 days. At this time necessary replacements of culture medium was performed, and also the growth state was microscopic controlled. Next, from each dish washed out dead cells by delicate replacement of the culture medium such as on the polymer surface left only living cells. Again, 0.5 ml of culture medium was applied to each of the dish, performing this with maximal launch force of the fluid from the automatic pipette. Culture medium above the polymer was collected with separated cells. The measurement of the amount of cells in the digital device for cells counting ADAM Mammalian Cell Counter (ADAM-MC) was performed. Number of cells in the measurement is inversely proportional to bonding force of polymer. The higher force, the higher therapeutic potential of the polymer.

TABLE

Results of performed comparative analysis.

| | Test of skinning over | Evaluation of viability after culturing on the selected substrate/ Functional analysis | Evaluation of viability after culturing on the selected substrate/ immunofluorescence analysis | Test of cells adhesion to the surface of polymer |
|---|---|---|---|---|
| Unwoven fabric 100% content DBC (34.8 g/m$^2$) | ++ | + | ++ | ++ |
| The single-layer dressing fully biodegradable made by leaching method, content DBC 100% (40.5 g/m$^2$) | ++ | +++ | +++ | +++++ |
| Example 1-5 Active element The single-layer dressing fully biodegradable | ++++ | +++++ | +++++ | ++ |
| Example 6-7 The single-layer dressing fully biodegradable made by leaching method | ++ | +++ | ++++ | +++++ |
| Example 8-9 The hydrogel dressing with suspended particles of chitin derivatives or their mixtures | +++ | ++++ | ++++ | ++ |
| Example 10-11 The hydrogel dressing with the particles of chitin derivatives or their mixtures on the surface of dressing | +++ | ++++ | ++++ | ++ |
| Example 12-15 The gel dressing of a porous structure based on chitin derivatives | +++ | +++ | ++++ | +++++ |
| Example 16 The single-layer dressing fully biodegradable made by leaching method enriched with cells (fibroblasts) | +++++ | +++++ | +++++ | +++++ |
| Example 17 The single-layer dressing fully biodegradable made by leaching method with the procedure of cells application | +++++ | +++++ | +++++ | +++++ |

+ the lowest: speed of skinning over, viability, bond strength to polymer
++
+++
++++
+++++ the highest: speed of skinning over, viability, bond strength to polymer As presented in the table, each of the tested dressings according to the invention shows better biologic functioning in relation to the reference dressing that is comprising active layer on the base of fibres from dibutyrylochitin, in the most performed tests in vitro (test of skinning over, evaluation of viability after culturing on the selected substrate/functional analysis, evaluation of viability after culturing on the selected substrate/immunofluorescence analysis). Only, the hydrogel dressing with the particles of chitin derivatives or their mixtures on the surface of dressing, the hydrogel dressing with suspended particles of chitin derivatives or their mixtures and the single-layer dressing fully biodegradable, show closed together biologic functioning in the test of cells adhesion to surface polymer and the single-layer dressing fully biodegradable made by leaching method content DBC 100% (40.5 g/m$^2$) and the single-layer dressing fully biodegradable made by leaching method in the test of skinning over. Additionally it should be underlined unexpected therapeutic effect of the single-layer dressing fully biodegradable, prepared by leaching method, enriched with cells (fibroblasts) and of the single-layer dressing fully biodegradable, prepared by leaching method together with the procedure of cells application, which showed the highest speed of skinning over, viability, as well as the bond strength to the polymer in all performed tests.

Performed studies allowed such modification of the active layer polymer of the dressings, to create the set of unique and application solutions of the different wounds. Moreover unknown and non-described until know in the world connection of bio-polymer with cells was performed. This resulted in obtaining of the dressing that repeatedly exceeded the unwoven dressing, and described functioning of cells and polymers after connection obtained synergic therapeutic effect.

The structure test of the active polymer layer 1 according to the invention in comparison with dressing material on the base of unwoven fabric was performed.

Figure 10:
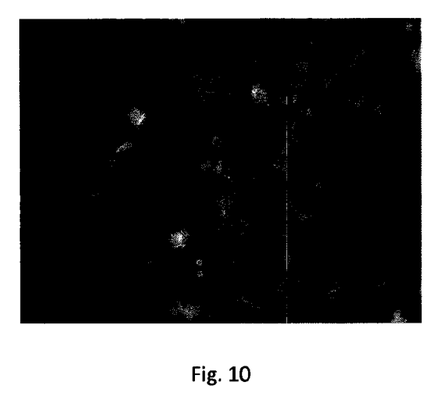
FIG. 10 shows a photo of a fluorescent microscope of a fragment of a woven dressing (fibrous) based on chitin derivative.

The photos presented in FIG. 10—are derived from fluorescence microscope NIKON Eclipse Ci-S and reversed optic microscope Olympus CKX41.

Figure 11:
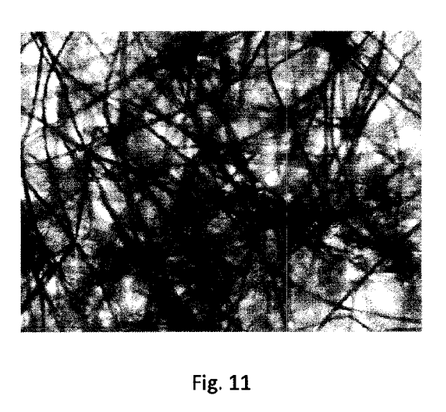
FIG. 11 shows a photo of an optic microscope of a fragment of a woven dressing (fibrous) based on chitin derivative.

The photo presented in FIG. 10 from fluorescence microscope (enlargement 10×10) illustrates a fragment of a woven dressing (fibrous) based on chitin derivative. The correct, adherent cells (with an average diameter of 25 μm) were applied on polymer skeleton, and their nuclei were dyed with a DAPI dye. The photo presented in FIG. 11 from the optic microscope (enlargement 4×10) illustrates the fragment of a woven dressing (fibrous) based on chitin derivative.

Figure 12:
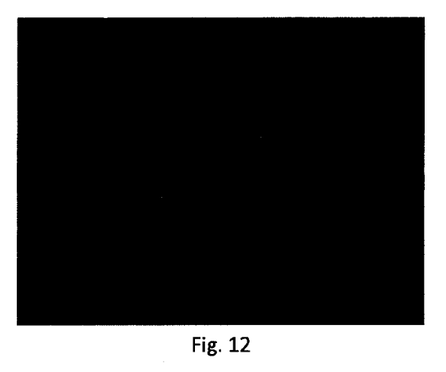
FIG. 12 shows a photo of a fluorescent microscope (enlargement 10×10) of a dressing fragment showing the piece of skeleton of the active polymer layer, three-dimensional based on chitin derivative prepared by leaching method.
Figure 13:
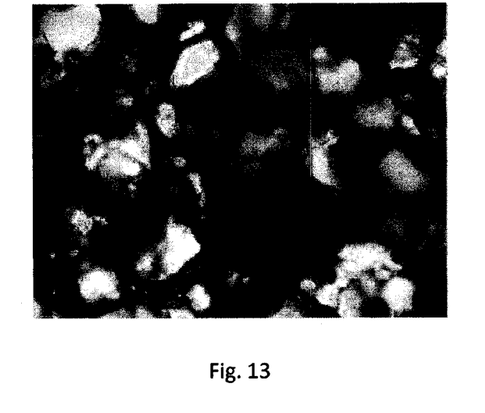
FIG. 13 shows a photo of an optic microscope (enlargement 4×10) of a dressing fragment prepared by leaching method based on chitin derivative.

The photo presented in FIG. 12 from fluorescence microscope (enlargement 10×10) of a dressing fragment showing the piece of skeleton of the active polymer layer, three-dimensional based on chitin derivative prepared by leaching method. The correct adherent cells (with an average diameter of 25 μm) were applied on polymer skeleton, and their nuclei were dyed with a DAPI dye. From the above photo results that the cells are arranged on a different, indicating the spatial structure of the tested dressing. The photo presented in FIG. 13 from the optic microscope (enlargement 4×10) of a dressing fragment prepared by leaching method based on chitin derivative.

Figure 14:
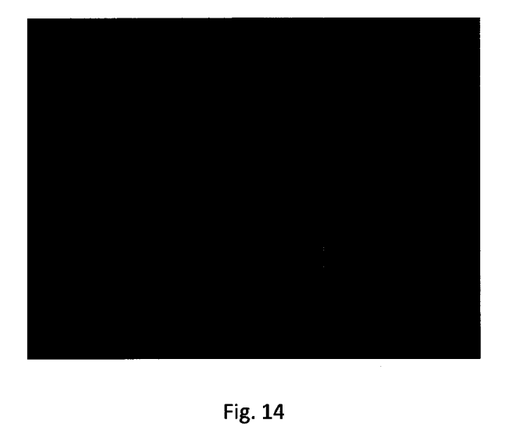
FIG. 14 shows a photo of a fluorescent microscope (enlargement 20×10) of a dressing fragment showing the piece of polymer three-dimensional skeleton based on chitin derivative prepared by leaching method and in the examples.

The photo presented in FIG. 14 from fluorescence microscope (enlargement 20×10) of a dressing fragment showing the piece of polymer three-dimensional skeleton based on chitin derivative prepared by leaching method. The photo of the three-dimensional skeleton of the dressing with a six pores, which size is from 2- to 4-times bigger than the thickness of the skeleton wall. The correct adherent cells with an average diameter of 25 μm were applied on polymer skeleton, which nuclei were dyed by means of DAPI. The above picture results in that the cells are arranged on different heights, indicating the spatial structure of the tested dressing. The cells coated the walls of the polymer skeleton, allowing for visualization of its three-dimensional structure.

The invention claimed is:

1. A single-layer wound dressing, comprising:
a free-standing, non-fibrous, fully biodegradable active polymer layer made of chitin ester derivatives obtained by a method comprising pouring out on a non-absorbing surface a solvent having dissolved therein at least one of the chitin derivatives obtained in the esterification reaction of chitin in the presence of aliphatic anhydrides of a chain of a length from C2 to C8 straight saturated.

2. The single-layer wound dressing according to claim 1, wherein a structure of the active polymer layer is made 100% of chitin ester derivatives.

3. The active polymer layer according to claim 1, wherein it is made of one chitin derivative, at a ratio from 0.1 to 100%, or a mixture of at least two chitin derivatives.

4. The active polymer layer according to claim 1, wherein it is porous.

5. The active polymer layer according to claim 1, wherein it is non-porous.

6. The active polymer layer according to claim 4, wherein it has pores of 0.1 mm to 4.0 mm in diameter, straight or coiled, depending on a wound type, or pores of a various size, in a single dressing ranges the pores percentage ratio from 1-90%.

7. The active polymer layer according to claim 2, wherein the active polymer is formed by pouring a solution of polymer selected from a group of chitin derivatives or mixture of chitin derivatives dissolved in an organic solvent on a uniformly spread water-soluble porogenic substance, $$\left(\frac{weight\_of\_polymer}{weight\_of\_porogenic\_agent} = from\ \frac{1}{5}\ to\ \frac{1}{40}\right)$$

with crystals of 100 to 800 μm in a mould, and then the solvent is evaporated at 24° C.-80° C., for 3-20 h, while the process of washing out the porogenic substance and solvent residues is done with water, for 1-24 h.

8. The active polymer layer according to claim 7, wherein the porogenic substance includes sodium chloride (NaCl).

9. The active polymer layer according to claim 7, wherein the organic solvent includes one or more of ketones and alkyl alcohols.

10. The active polymer layer according to claim 7, wherein a concentration of chitin derivative/mixture of chitin derivatives in solvent is 0.01-0.4 g/ml, preferably 0.001-0.15 g/ml.

11. The active polymer layer according to claim 1, wherein it is saturated with excipients.

12. The active polymer layer according to claim 11, wherein the excipients include one or more of silver ions Ag÷(0.01-5%), potassium ions K(÷((0.01-2%), calcium ions Ca2÷(0.01-2%), Zn2÷ions (0.01-1,5%), citric acid (0.001-5%), and bismuth salts (0.001-5%).

13. The active polymer layer according to claim 1, wherein it is saturated with antiseptic substances.

14. The active polymer layer according to claim 13, wherein the antiseptic substances include one or more of: neomycin, polymyxin B, bacitracin, vancomycin, gentamycin, cephalosporin and other wide-spectrum antibiotics.

15. The active polymer layer according to claim 1, wherein it is saturated with metronidazole.

16. The active polymer layer according to claim 1, wherein it comprises fibroblasts and/or keratinocytes.

17. The active polymer layer according to claim 1, wherein the aliphatic anhydrides of a chain of a length from C2 to C8 straight saturated comprise valeric anhydride.

* * * * *